(12) United States Patent
Kitamura et al.

(10) Patent No.: US 8,349,593 B2
(45) Date of Patent: Jan. 8, 2013

(54) PROCESS FOR PRODUCTION OF SUCCINIC ACID AMIDE COMPOUND

(75) Inventors: Toru Kitamura, Ebetsu (JP); Hiroshi Soejima, Ebetsu (JP); Tamizi Sugiyama, Chofu (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 114 days.

(21) Appl. No.: 12/739,841

(22) PCT Filed: Oct. 24, 2008

(86) PCT No.: PCT/JP2008/003013
§ 371 (c)(1),
(2), (4) Date: Apr. 26, 2010

(87) PCT Pub. No.: WO2009/054138
PCT Pub. Date: Apr. 30, 2009

(65) Prior Publication Data
US 2010/0248314 A1 Sep. 30, 2010

(30) Foreign Application Priority Data
Oct. 26, 2007 (JP) .................................. 2007-279376

(51) Int. Cl.
*C12P 13/02* (2006.01)
*C12P 17/10* (2006.01)
*C12P 17/12* (2006.01)
*C12P 1/04* (2006.01)
*C12P 1/00* (2006.01)

(52) U.S. Cl. .......... 435/129; 435/41; 435/121; 435/122; 435/170

(58) Field of Classification Search ........................ None
See application file for complete search history.

(56) References Cited

FOREIGN PATENT DOCUMENTS
JP 11-255607 A 9/1999
JP 2001-139405 A 5/2001

OTHER PUBLICATIONS

Taraz et al. BioMetals 12: 323-329, 1999.*
Budzikiewiez, "Secondary metabolites from flourescent pseudomonads," FEMS Microbiology Reviews 104, 1993, pp. 209-228.
International Search Report for International Patent Application No. PCT/JP2008/003013, mailed on Jan. 27, 2009.
Itagaki et al., "Indole or naphtalene substituted compounds of N-(phenethyl)succiamic acid derivatives exhibit root-promoting activity," Article of Crop Science Society of Japan, Japanese Journal of Crop Science, vol. 70, No. 1, 2001, pp. 190-191.
Notice of Reason for Rejection for corresponding Japanese Patent Application No. 2007-279376, dated May 22, 2012.
Soejima et al., "Purification and isolation of root-promoting substance, N-(phenethyl)succinamic acid," Article of Crop Science Society of Japan, Japanese Journal of Crop Science, vol. 60, No. 1, 2000, pp. 186-187.

* cited by examiner

*Primary Examiner* — Anand Desai
*Assistant Examiner* — Iqbal H Chowdhury
(74) *Attorney, Agent, or Firm* — Birch, Stewart, Kolasch & Birch, LLP

(57) ABSTRACT

Disclosed is a novel process for producing a compound represented by the general formula (1) by using a microorganism, wherein the compound is useful as a plant growth stimulant. Specifically disclosed is a process for producing a succinic acid amide compound represented by the general formula (1) [wherein Ar represents a phenyl, naphthyl or indolyl group which may have a substituent; and n represents a numeral value ranging from 1 to 4] or a salt thereof, which is characterized by culturing a microorganism of the genus *Pseudomonas* that is capable of synthesizing a succinic acid amide in a culture medium containing an arylalkylamine represented by the general formula (2).

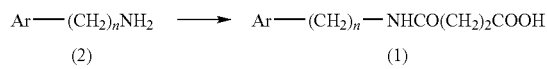

2 Claims, No Drawings

PROCESS FOR PRODUCTION OF SUCCINIC ACID AMIDE COMPOUND

TECHNICAL FIELD

The present invention relates to a process for producing a succinic acid amide compound useful as a plant growth stimulant by using a microorganism.

BACKGROUND ART

In agricultural and forestry sectors, there has been a strong desire for a component having high root-promoting activity and promoting plant growth, and many studies have been done. Under such circumstances, it is known that a succinic acid amide compound represented by the following general formula (1):

$$Ar—(CH_2)_n—NHCO(CH_2)_2COOH \quad (1)$$

wherein Ar represents an optionally substituted phenyl, naphthyl or indolyl group; and n is an integer of 1 to 4, or a salt thereof has an excellent root-promoting activity and is useful as a plant growth regulator (Patent Documents 1 and 2).

It is known that this succinic acid amide compound is produced by a microorganism belonging to the genus *Bacillus*, though it can also be obtained by chemical synthesis as described in Patent Documents 1 and 2 (non-Patent Document 1)

Patent Document 1: JP 1-255607 A
Patent Document 2: JP 2001-139405 A
non-Patent Document 1: Soejima et al., 1999, Isolation and purification of novel root-promoting substance N-(phenethyl)succinic acid amide, The Japanese Society for Chemical Regulation of Plants, the 34th Meeting Koen Yoshishu, pages 75-76
non-Patent Document 2: Environmental Health Bureau Ministry of Health and Welfare (Ed.) 1990, Chapter microbial food hygiene inspection guidelines, Japan Food Hygiene Association

DISCLOSURE OF THE INVENTION

Problems to be Solved by the Invention

Although almost all the presently marketed plant growth regulators are produced by chemical synthesis, there still remains a strong trend that consumers have doubt about the chemical safety. This is supported by the fact that organic farm products as well as farm produtcts by cultivation with reduced pesticide are lionized. In this respect, as for pesticides inclusive plant growth regulators, those of natural origin are preferred, and the demanded products are not chemically synthesized products, but products produced by microorganisms. However, conventional techniques use microorganisms of the genus *Bacillus*, typical aerobic spore-forming bacteria, and are disadvantageous in that the handling is difficult. That is, there are disadvantages such as high risk of environmental pollution in addition to the difficulty in sanitation after using an apparatus because endospores formed during culturing microorganisms of the genus *Bacillus* have strong resistance to heat, dryness, radiation and chemicals (non-Patent Document 2).

Therefore, an object of the present invention is to provide a novel process for producing a compound represented by the above general formula (1) which is useful as a plant growth accelerator by a microorganism other than that of the genus *Bacillus*.

Means for Solving the Problems

The present inventors have investigated novel microorganisms capable of producing the compound of the general formula (1), and have found that a microorganism of the genus *Pseudomonas*, which is taxonomically-distinct from microorganisms of the genus *Bacillus* and completely lacks spore-forming capability, has a capability to produce a compound of the general formula (1) from an arylalkylamine, resulting in completion of the present invention.

That is, the present invention provides a process for producing a succinic acid amide compound represented by the general formula (1):

$$Ar—(CH_2)_n—NHCO(CH_2)_2COOH \quad (1)$$

wherein Ar represents an optionally substituted phenyl, naphthyl or indolyl group; and n represents an integer of 1 to 4, or a salt thereof, which comprises culturing a microorganism of the genus *Pseudomonas* that is capable of synthesizing a succinic acid amide in a culture medium containing an arylalkylamine represented by the general formula (2):

$$Ar—(CH_2)_nNH_2 \quad (2)$$

wherein Ar and n are as defined above.

Effects of the Invention

According to the process of the present invention, the succinic acid amide compound or a salt thereof which is useful as a plant growth regulator can be efficiently produced by culturing a microorganism of the genus *Pseudomonas*.

BEST MODE FOR CARRYING OUT THE INVENTION

While the microorganism used in the present invention is not particularly limited as far as it belongs to the genus *Pseudomonas* and is capable of synthesizing the succinic acid amide compound, examples thereof include microorganisms belonging to *Pseudomonas koreensis*, *Pseudomonas fluorescens*, *Pseudomonas abietaniphila*, *Pseudomonas aeruginosa*, *Pseudomonas agarici*, *Pseudomonas alcaligenes*, *Pseudomonas alcaliphila*, *Pseudomonas amygdali*, *Pseudomonas anguilliseptica*, *Pseudomonas asplenii*, *Pseudomonas aurantiaca*, *Pseudomonas avellanae*, *Pseudomonas azotifigens*, *Pseudomonas azotoformans*, *Pseudomonas balearica*, *Pseudomonas beijerinckii*, *Pseudomonas boreopolis*, *Pseudomonas brassicacearum*, *Pseudomonas brenneri*, *Pseudomonas cannabina*, *Pseudomonas carboxydohydrogena*, *Pseudomonas caricapapayae*, *Pseudomonas cedrina*, *Pseudomonas chloritidismutans*, *Pseudomonas chlororaphis*, *Pseudomonas cichorii*, *Pseudomonas cissicola*, *Pseudomonas citronellolis*, *Pseudomonas corrugata*, *Pseudomonas costantinii*, *Pseudomonas cremoricolorata*, *Pseudomonas denitrificans*, *Pseudomonas elongata*, *Pseudomonas extremorientalis*, *Pseudomonas ficuserectae*, *Pseudomonas flavescens*, *Pseudomonas flectens*, *Pseudomonas fragi*, *Pseudomonas frederiksbergensis*, *Pseudomonas fluva*, *Pseudomonas fuscovaginae*, *Pseudomonas gelidicola*, *Pseudomonas geniculata*, *Pseudomonas gessardii*, *Pseudomonas graminis*, *Pseudomonas grimontii*, *Pseudomonas halophila*, *Pseudomonas hibiscicola*, *Pseudomonas huttiensis*, *Pseudomonas indica*, *Pseudomonas jessenii*, *Pseudomonas jinjuensis*, *Pseudomonas kilonensis*, *Pseudomonas lanceolate*, *Pseudomonas libanensis*, *Pseudomonas lini*, *Pseudomonas lundensis*, *Pseudomonas luteola*, *Pseudomonas mandelii*, *Pseudomo-* nas marginalis, Pseudomonas mediterranea, Pseudomonas meliae, Pseudomonas mendocina, Pseudomonas mephitica, Pseudomonas migulae, Pseudomonas monteilii, Pseudomonas mosselii, Pseudomonas mucidolens, Pseudomonas multiresinivorans, Pseudomonas nitroreducens, Pseudomonas oleovorans, Pseudomonas orientalis, Pseudomonas oryzihabitans, Pseudomonas pachastrellae, Pseudomonas palleroniana, Pseudomonas parafulva, Pseudomonas pertucinogena, Pseudomonas pictorum, Pseudomonas plecoglossicida, Pseudomonas pseudoalcaligenes, Pseudomonas psychrophila, Pseudomonas putida, Pseudomonas resinovorans, Pseudomonas rhodesiae, Pseudomonas saccharophila, Pseudomonas salomonii, Pseudomonas savastanoi, Pseudomonas spinosa, Pseudomonas straminea, Pseudomonas stutzeri, Pseudomonas synxantha, Pseudomonas syringae, Pseudomonas syzygii, Pseudomonas taetrolens, Pseudomonas thermotolerans, Pseudomonas thivervalensis, Pseudomonas tolaasii, Pseudomonas tremae, Pseudomonas umsongensis, Pseudomonas vancouverensis, Pseudomonas veronii, Pseudomonas viridiflava, and Pseudomonas xanthomarina. Among them, microorganisms of Pseudomonas koreensis and Pseudomonas fluorescens are particularly preferred.

Specific examples of the microorganism used in the process of the present invention include Pseudomonas koreensis AR15, Pseudomonas koreensis JCM14769, Pseudomonas fluorescens RCH38-2, Pseudomonas fluorescens CH17-15, Pseudomonas fluorescens CH34-8, Pseudomonas fluorescens CH34-11 and Pseudomonas fluorescens JCM5963. Among these microbial strains, Pseudomonas koreensis JCM14769 and Pseudomonas fluorescens JCM5963 can be purchased from Independent Administrative Institution RIKEN, BioResource Center, Microbe Division. The other microbial strains are those isolated from soil.

In order to produce the succinic acid amide compound represented by the general formula (1) or a salt thereof by using these microorganisms, the arylalkylamine represented by the general formula (2) is added to a culture medium. Ar in the general formulas (1) and (2) represents a phenyl group, a naphthyl group or an indolyl group each of which may be substituted. Among them, a phenyl group or an indolyl group is preferred, and a phenyl group or a 3-indolyl group is particularly preferred.

Examples of a member with which the phenyl, naphthyl or indolyl group may be substituted include one to five selected from a halogen atom, a hydroxy group, a nitro group, a $C_{1-6}$ alkyl group, and $C_{1-6}$ alkoxy group. Examples of the halogen atom include a fluorine atom, a chlorine atom, a bromine atom, and an iodine atom. Examples of the $C_{1-6}$ alkyl group include a methyl group, an ethyl group, an isopropyl group, and a t-butyl group. Examples of the $C_{1-6}$ alkoxy group include a methoxy group, an ethoxy group, and an isopropyloxy group.

In the general formulas (1) and (2), n represents an integer of 1 to 4, preferably 1 to 3, in particular 2.

In the general formulas (1) and (2), a phenyl group or an indolyl group is particularly preferred as Ar, and particularly preferred n is 2.

In view of the productivity of the succinic acid amide compound, the content of the arylalkylamine (2) in a culture medium is preferably 0.001 to 10% by weight, more preferably 0.001 to 5% by weight, in particular, 0.01 to 5% by weight.

In the process of the present invention, the above microorganism of the genus Pseudomonas can be cultured under conventional conditions for growing a microorganism of the genus Pseudomonas except for addition of the arylalkylamine (2) to a culture medium. Preferably, ingredients required for the growth of a microorganism of the genus Pseudomonas such as carbon source, nitrogen source, vitamin source and mineral source are added to a culture medium. Examples of the carbon source to be used include glucose, starch syrup and soluble starch. Examples of the nitrogen source to be used include yeast extract, peptone, meat extract, corn steep liquor, amino acid solution, soybean meal, ammonium sulfate and ammonium chloride. Examples of the mineral source to be used include magnesium salts, potassium salts, phosphates and iron salts. Usually, a liquid culture medium can be used as the culture medium, and the culture can be carried out by shaking culture or spinner culture.

Preferably, the culture is carried out at 8 to 45° C., pH 3.2 to 9.5 under aerobic conditions. The culture time can be 24 to 240 hours.

The succinic acid amide compound (1) or a salt thereof can be collected by a conventional method because the succinic acid amide compound (1) or a salt thereof is accumulated in the culture medium by the above culture. While this culture medium itself can be used as a plant growth regulator or a fertilizer, the succinic acid amide compound (1) or a salt thereof can be purified from the culture medium. Examples of the purification method to be employed include concentration of the culture medium, precipitation, extraction with an organic solvent and various chromatographic methods.

EXAMPLES

The following Examples illustrate the present invention in detail but the present invention is not limited thereto.

Example 1

Ten 500-mL baffled Erlenmeyer flasks each of which contained 300 mL of 0.1% phenethylamine-added Potato Dextrose Broth (manufacture by Difco, hereinafter abbreviated as PDB) were autoclaved. Each flask was inoculated with Pseudomonas koreensis AR-15 strain (derived from soil of Iwate Prefecture), which had been pre-cultured in advance in PDB, and subjected to shaking culture at 27° C., 80 rpm for 10 days.

The resulting culture medium was roughly purified as follows. The culture medium was centrifuged at 6,500 rpm for 30 minutes and the supernatant was adjusted to pH 3.0 with hydrochloric acid. Separately, styrene-divinylbenzene synthetic adsorption resin DIAION HP-20 was washed with methanol, and then a column (inner diameter 18 mm×length 300 mm) was packed with the washed resin, followed by passing an aqueous acetic acid solution at pH 3.0 therethrough. The above supernatant was passed through the column to adsorb N-phenethyl succinic acid amide (hereinafter abbreviated as PESA). After washing the column with 1 L of 10% isopropanol, PESA was eluted with 1 L of 30% isopropanol. The eluate was concentrated to about 500 mL with an evaporator, adjusted to pH 8.0 with an aqueous sodium hydroxide solution, and extracted three times with ethyl acetate. The ethyl acetate layers were discarded. The remaining aqueous phase was adjusted to pH 2.5 with hydrochloric acid and extracted three times with ethyl acetate. The ethyl acetate layer thus obtained was dehydrated over anhydrous magnesium sulfate, and the solvent was removed under reduced pressure. The residue was dissolved in a small amount of 1N aqueous acetic acid solution and passed through a SepPak C18 cartridge (manufactured by Waters) prepared by washing and passing 1N aqueous acetic acid solution therethrough to adsorb PESA. The cartridge was eluted with 20 mL of 60% methanol and the eluate was evaporated to dryness under reduced pressure.

A sample thereof was purified by HPLC [column: ODS-A, inner diameter 10 mm×length 250 mm (manufactured by YMC); mobile phase: 1% acetic acid-containing 40% methanol; flow rate: 3.0 mL/min.] to obtain a fraction corresponding to PESA retention time (retention time: 11-14 minutes). Further, the fraction thus obtained was purified by HPLC [column: XTerra RP18, inner diameter 10 mm×length 250 mm (manufactured by Waters); mobile phase: 1% acetic acid-containing 45% methanol; flow rate: 3.0 mL/min.] to obtain a fraction corresponding to PESA retention time (retention time: 9-12 minutes). Further, the fraction thus obtained was purified by HPLC [column: XTerra RP18, inner diameter 10 mm×length 250 mm (manufactured by Waters); mobile phase: 1% acetic acid-containing 25% acetonitrile; flow rate: 3.0 mL/min.] to obtain a fraction corresponding to PESA retention time (retention time: 11-14 minutes). Furthermore, the fraction thus obtained was purified by HPLC [column: SymmetryShield RP18, inner diameter 4.6 mm×length 250 mm (manufactured by Waters); column temperature: 40° C.; mobile phase: 1% acetic acid-containing 20% acetonitrile; flow rate: 0.8 mL/min.] to obtain a fraction corresponding to PESA retention time (retention time: 11-13 minutes.). Moreover, the fraction thus was purified by HPLC [column: YMC Pack Ph, inner diameter 4.6 mm×length 250 mm (manufactured by YMC); column temperature: 40° C.; mobile phase: 1% acetic acid-containing 40% methanol; flow rate: 0.8 mL/min.] to obtain a fraction corresponding to PESA retention time (retention time: 11.5-14 minutes) as a single peak. The fraction thus obtained was concentrated under reduced pressure and dried under reduced pressure in the presence of diphosphorus pentaoxide in a desiccator to obtain 1 mg of crystals of PESA. When the crystals were analyzed by mass spectrometry (MS-FAB) using glycerol, $(M+H)^+$ was 222.1 and $(M+Na)^+$ was 244.8, which were identical with the chemical synthetic standard. Further, the results of $^1$H-NMR also showed that they were identical with the chemical synthetic standard (Table 1). These results showed that the above microbial strain produced 0.33 mg/L of PESA in the culture medium.

TABLE 1

| | Mass (FAB, M + 1) | $^1$H-NMR (300 MHz, CD$_3$OD, δ ppm) |
|---|---|---|
| Chemical synthetic standard | 222 | 7.28-7.16 (5H, m), 3.40-3.35 (2H, m), 2.79-2.74 (2H, m), 2.58-2.53 (2H, m), 2.44-2.40 (2H, m) |
| Crystals isolated from culture medium | 222 | 7.29-7.16 (5H, m), 3.39-3.33 (2H, m), 2.79-2.74 (2H, m), 2.53-2.48 (2H, m), 2.43-2.38 (2H, m) |

Example 2

According to the same manner as that described in Example 1, the culture and rough purification were carried out except that the culture medium was replaced with 0.1% tryptamine-added PDB and the culture medium number were 300 mL×2.

A sample was purified by HPLC [column: ODS-A, inner diameter 10 mm×length 250 mm (manufactured by YMC); mobile phase: 1% acetic acid-containing 50% methanol; flow rate: 3.0 mL/min.] to obtain a fraction corresponding to the retention time of N-[[2-(3-indolyl)ethyl]succinic acid amide (hereinafter abbreviated as IESA) (retention time: 11.0-14.5 minutes). Further, the fraction thus obtained was purified by HPLC [column: YMC Pack Ph, inner diameter 10 mm×length 250 mm (manufactured by YMC); mobile phase: 1% acetic acid-containing 50% methanol; flow rate: 3.0 mL/min.] to obtain a fraction corresponding the retention time of IESA (retention time: 9-12 minutes). Furthermore, the fraction thus obtained was analyzed by HPLC [column: SymmetryShield RP18, inner diameter 4.6 mm×length 250 mm (manufactured by Waters); column temperature: 40° C.; mobile phase: 1% acetic acid-containing 40% methanol; flow rate: 0.8 mL/min.). A peak was recognized at 11.85 minutes and this was approximately identical with chemical synthetic IESA. When UV absorption spectrum of this peak was measured, a maximum absorption was recognized at 281 nm. This was identical with chemical synthetic IESA. When the peak area measured at 280 nm was compared with a calibration curve prepared by using chemical synthetic IESA, the amount of IESA obtained was calculated as 0.058 mg. These results showed that the above strain produced 0.095 mg/L of IESA in the culture medium.

Example 3

According to the same manner as that described in Example 1, the culture and rough purification were carried out except that the microbial strain was replaced with *Pseudomonas koreensis* JCM14769 strain.

A sample was purified by HPLC [column: ODS-A, inner diameter 10 mm×length 250 mm (manufactured by YMC); mobile phase: 1% acetic acid-containing 50% methanol; flow rate: 3.0 mL/min.] to obtain a fraction corresponding to the retention time of PESA (retention time: 11.5-14.0 minutes). Further, the fraction thus obtained was purified by HPLC [column: YMC Pack Ph, inner diameter 10 mm×length 250 mm (manufactured by YMC); mobile phase: 1% acetic acid-containing 50% methanol; flow rate: 3.0 mL/min.] to obtain a fraction corresponding to the retention time of PESA (retention time: 9-11.5 minutes). Furthermore, the fraction thus obtained was purified by HPLC [column: XTerra RP18, inner diameter 10 mm×length 250 mm (manufactured by Waters); mobile phase: 1% acetic acid-containing 30% acetonitrile; flow rate: 3.0 mL/min.] to obtain a fraction corresponding to the retention time of PESA (retention time: 8.0-10.5 minutes). Moreover, the fraction thus obtained was analyzed by HPLC [column: SymmetryShield RP18, inner diameter 4.6 mm×length 250 mm (manufactured by Waters); column temperature: 40° C.; mobile phase: 1% acetic acid-containing 40% methanol; flow rate: 0.8 mL/min.]. A peak was recognized at 11.88 minutes and this was approximately identical with chemical synthetic PESA. When UV absorption spectrum of this peak was measured, a maximum absorption was recognized at 260 nm. This was identical with chemical synthetic PESA. When the peak area measured at 260 nm was compared with a calibration curve prepared by using chemical synthetic PESA, the amount of PESA obtained was calculated as 0.30 mg. These results showed that the above strain produced 0.1 mg/L of PESA in the culture medium.

Example 4

According to the same manner as that described in Example 3, the culture, rough purification and analysis were carried out except that the microbial strain was replaced with *Pseudomonas fluorescens* RCH38-2 strain (derived from soil of Hokkaido, Japan) and the culture medium number was 300 mL×2.

A peak was recognized at 11.50 minutes and this was approximately identical with chemical synthetic PESA. When UV absorption spectrum of this peak was measured, a maximum absorption was recognized at 259 nm. This was identical with chemical synthetic PESA. When the peak area measured at 260 nm was compared with a calibration curve prepared by using chemical synthetic PESA, the amount of PESA obtained was calculated as 0.45 mg. These results showed that the above strain produced 0.75 mg/L of PESA in the culture medium.

Example 5

According to the same manner as that described in Example 3, the culture, rough purification and analysis were carried out except that the microbial strain was replaced with *Pseudomonas fluorescens* JCM596 strain and the amount of the culture medium was 4.2 L.

A peak was recognized at 11.65 minutes and this was approximately identical with chemical synthetic PESA. When UV absorption spectrum of this peak was measured, a maximum absorption was recognized at 259 nm. This was identical with chemical synthetic PESA. When the peak area measured at 260 nm was compared with a calibration curve prepared by using chemical synthetic PESA, the amount of PESA obtained was calculated as 1.22 mg. These results showed that the above strain produced 0.29 mg/L of PESA in the culture medium.

The invention claimed is:

1. A process for producing, a succinic acids amide compound represented by the general formula (1):

$$Ar-(CH_2)_n-NHCO(CH_2)_2COOH \quad (1)$$

wherein Ar represents an optionally substituted phenyl group; and n represents an integer of 1 to 4, or a salt thereof, which comprises culturing a microorganism of the genus *Pseudomonas* that is synthesizes a succinic acid amide in a culture medium containing an arylalkylamine represented by the general formula (2):

$$Ar-(CH_2)_nNH_2 \quad (2)$$

wherein Ar and n are as defined above and purifying succinic acid amide.

2. The process according to claim 1, wherein Ar is a phenyl group, and n is 2.

* * * * *